US009051343B2

(12) United States Patent
Gless, Jr. et al.

(10) Patent No.: US 9,051,343 B2
(45) Date of Patent: Jun. 9, 2015

(54) PHOSPHATE ESTERS OF NORIBOGAINE

(71) Applicant: DemeRx, Inc., Miami, FL (US)

(72) Inventors: Richard D. Gless, Jr., Oakland, CA (US); Robert M. Moriarty, Michiana Shores, IN (US)

(73) Assignee: DEMERX, INC., Miami, FL (US)

( * ) Notice: Subject to any disclaimer, the term of this patent is extended or adjusted under 35 U.S.C. 154(b) by 151 days.

(21) Appl. No.: 13/708,837

(22) Filed: Dec. 7, 2012

(65) Prior Publication Data
US 2013/0165414 A1 Jun. 27, 2013

Related U.S. Application Data

(60) Provisional application No. 61/569,150, filed on Dec. 9, 2011.

(51) Int. Cl.
| | | |
|---|---|---|
| *A61K 31/55* | (2006.01) | |
| *C07D 487/22* | (2006.01) | |
| *C07F 9/6561* | (2006.01) | |

(52) U.S. Cl.
CPC ............ *C07F 9/6561* (2013.01); *C07D 487/22* (2013.01)

(58) Field of Classification Search
USPC ...................................... 514/214.02; 540/579
See application file for complete search history.

(56) References Cited

U.S. PATENT DOCUMENTS

| | | | |
|---|---|---|---|
| 2,813,873 | A | 11/1957 | Janot et al. |
| 3,516,989 | A | 6/1970 | Sallay |
| 3,557,126 | A | 1/1971 | Sallay |
| 3,574,220 | A | 4/1971 | Sallay |
| 3,639,408 | A | 2/1972 | Nagata et al. |
| 3,715,361 | A | 2/1973 | Epstein et al. |
| 3,875,011 | A | 4/1975 | Rubenstein et al. |
| 4,107,288 | A | 8/1978 | Oppenheim et al. |
| 4,272,541 | A | 6/1981 | Kotick et al. |
| 4,375,414 | A | 3/1983 | Strahilevitz |
| 4,444,758 | A | 4/1984 | Scherschlicht et al. |
| 4,462,941 | A | 7/1984 | Lee et al. |
| 4,464,378 | A | 8/1984 | Hussain |
| 4,499,096 | A | 2/1985 | Lotsof |
| 4,573,995 | A | 3/1986 | Chen et al. |
| 4,587,243 | A | 5/1986 | Lotsof |
| 4,604,365 | A | 8/1986 | O'Neill et al. |
| 4,620,977 | A | 11/1986 | Strahilevitz |
| 4,626,539 | A | 12/1986 | Aungst et al. |
| 4,661,492 | A | 4/1987 | Lewis et al. |
| 4,668,232 | A | 5/1987 | Cordes et al. |
| 4,737,586 | A | 4/1988 | Potier et al. |
| 4,806,341 | A | 2/1989 | Chien et al. |
| 4,857,523 | A | 8/1989 | Lotsof |
| 5,026,697 | A | 6/1991 | Lotsof |
| 5,075,341 | A | 12/1991 | Mendelson et al. |
| 5,145,684 | A | 9/1992 | Liversidge et al. |
| 5,149,538 | A | 9/1992 | Granger et al. |
| 5,152,994 | A | 10/1992 | Lotsof |
| 5,283,247 | A | 2/1994 | Dwivedi et al. |
| 5,290,784 | A | 3/1994 | Qu et al. |
| 5,316,759 | A | 5/1994 | Rose et al. |
| 5,382,657 | A | 1/1995 | Karasiewicz et al. |
| 5,426,112 | A | 6/1995 | Zagon et al. |
| 5,552,406 | A | 9/1996 | Mendelson et al. |
| 5,574,052 | A | 11/1996 | Rose et al. |
| 5,578,645 | A | 11/1996 | Askanazi et al. |
| 5,580,876 | A | 12/1996 | Crain et al. |
| 5,591,738 | A | 1/1997 | Lotsof |
| 5,618,555 | A | 4/1997 | Tokuda et al. |
| 5,703,101 | A | 12/1997 | Rose et al. |
| 5,726,190 | A | 3/1998 | Rose et al. |
| 5,760,044 | A | 6/1998 | Archer |
| 5,861,422 | A | 1/1999 | Rose et al. |
| 5,865,444 | A | 2/1999 | Kempf et al. |
| 5,925,634 | A | 7/1999 | Olney |
| 5,935,975 | A | 8/1999 | Rose et al. |
| 6,211,360 | B1 | 4/2001 | Glick et al. |
| 6,291,675 | B1 | 9/2001 | Coop et al. |
| 6,348,456 | B1 | 2/2002 | Mash et al. |
| 6,451,806 | B2 | 9/2002 | Farrar |
| 6,806,291 | B1 | 10/2004 | Sunkel et al. |
| 6,864,271 | B2 | 3/2005 | Bazan et al. |
| 7,220,737 | B1 | 5/2007 | Mash |
| 7,737,169 | B2 | 6/2010 | Corrie et al. |
| 7,745,479 | B2 | 6/2010 | Nettekoven et al. |
| 7,754,710 | B2 | 7/2010 | Mash |
| 8,178,524 | B2 | 5/2012 | Mash |
| 8,362,007 | B1 | 1/2013 | Mash et al. |

(Continued)

FOREIGN PATENT DOCUMENTS

| | | |
|---|---|---|
| CA | 2039197 | 9/1995 |
| DE | 22 17 132 | 10/1972 |

(Continued)

OTHER PUBLICATIONS

Bloomer et al., "Arc/Arg3.1 Translation Is controlled by Convergent N-Methyl-D-aspartate and Gs-coupled Receptor Signaling Pathways," J. Bio. Chem. (2008), 283(1):582-592.
Huffman et al., "A Formal Synthesis of (±)-Ibogamine," J. Org. Chem., (1985), 50:1460-1464.
PCT International Search Report and Written Opinion in related PCT Patent Application No. PCT/US2012/67799, Mar. 28, 2013.
Suvarna et al., "Hydrolysis of N-Methyl-D-aspartate Receptor-Stimulated cAMP and cGMP by PDE4 and PDE2 Phosphodiesterases in Primary Neuronal Cultures of Rat Cerebral Cortex and Hippocampus," J. Pharmacol. Exp. Ther., (2002), 302(1):249-256.
U.S. Appl. No. 13/165,639, filed Jun. 21, 2011, Mash et al.
U.S. Appl. No. 13/566,819, filed Aug. 3, 2012, Mash et al.
U.S. Appl. No. 14/257,841, filed Apr. 21, 2014, Mash, Deborah C.
U.S. Appl. No. 14/298,534, filed Jun. 6, 2014, Mash et al.
U.S. Appl. No. 14/323,743, filed Jul. 3, 2014, Mash et al.
Al-Shabanah et al. "Gastric Antiulcer and Cytoprotective Effects of Cathinone, a Psychoactive Alkaloid of Khat (Catha Edulis Forsk.) And Amphetamine in Rats", Regulatory Peptides, abstract only, 1994.

(Continued)

*Primary Examiner* — Brenda Coleman
(74) *Attorney, Agent, or Firm* — Foley & Lardner LLP

(57) ABSTRACT

Disclosed herein are phosphate esters of noribogaine and dihydronoribogaine, and esters and pharmaceutically acceptable salts thereof, pharmaceutical compositions comprising such compounds, and the methods of their use, including in the treatment of addiction and/or pain.

7 Claims, No Drawings

(56) References Cited

U.S. PATENT DOCUMENTS

| | | | |
|---|---|---|---|
| 8,637,648 | B1 | 1/2014 | Mash et al. |
| 8,741,891 | B1 * | 6/2014 | Mash .................. 514/214.02 |
| 8,765,737 | B1 | 7/2014 | Mash et al. |
| 2003/0153552 | A1 | 8/2003 | Mash et al. |
| 2003/0158202 | A1 | 8/2003 | Caldirola et al. |
| 2006/0051317 | A1 | 3/2006 | Batrakova et al. |
| 2009/0264653 | A1 | 10/2009 | Bartolini et al. |
| 2010/0249105 | A1 | 9/2010 | Schrimpf et al. |
| 2010/0311722 | A1 | 12/2010 | Mash |
| 2010/0311723 | A1 | 12/2010 | Mash |
| 2010/0311725 | A1 | 12/2010 | Mash |
| 2012/0083485 | A1 | 4/2012 | Mash |
| 2013/0072472 | A1 | 3/2013 | Gless et al. |
| 2013/0131046 | A1 | 5/2013 | Moriarty et al. |
| 2013/0303756 | A1 | 11/2013 | Mash et al. |
| 2014/0113878 | A1 | 4/2014 | Mash et al. |
| 2014/0179684 | A1 | 6/2014 | Mash et al. |
| 2014/0179685 | A1 | 6/2014 | Mash et al. |

FOREIGN PATENT DOCUMENTS

| | | |
|---|---|---|
| GB | 0 841 697 | 7/1960 |
| GB | 0 924 042 | 4/1962 |
| GB | 1 256 914 | 12/1971 |
| GB | 1 378 348 | 12/1974 |
| GB | 2 271 059 | 4/1994 |
| JP | 04-221315 | 8/1992 |
| WO | WO-91/18609 A1 | 12/1991 |
| WO | WO-93/20825 A1 | 10/1993 |
| WO | WO-93/25217 A1 | 12/1993 |
| WO | WO-94/06426 A1 | 3/1994 |
| WO | WO-94/14490 A1 | 7/1994 |
| WO | WO-96/03127 A1 | 2/1996 |

OTHER PUBLICATIONS

Ala-Hurula et al. "Tolfenamic Acid and Ergotamine Abuse", Headache: The Journal of Head and Face Pain, 21(6): abstract only, 1981.

Ala-Hurula et al. "Erogotamine Abuse: Results of Ergotamine Discontinuation, with Special Reference to the Plasma Concentrations", Cephalalgia, 2:4: abstract only, 1982.

Alexander. "A Procedure for Drug Screening Without the Need to Transport Urines Use of Ion Exchange Papers and Hem Agglutination Inhibition", Clin Toxicol, 9(3): abstract only, 1976.

Alim et al. "Open-Label, Dose Run-Up Study of Diethylpropion in Initial Cocaine Abstinence", Clinical Neuropharmacology, 17(2): abstract only, 1994.

Almeida. "Use and Abuse of Alcohol and Drugs a Clinical Study of Certain Aspects of Their Interrelationship", Bol of Sanit Panam, 88(1), abstract only, 1980.

Azevedo et al. "Adrenergic Nerve Degeneration Induced by Condensation Products of Adrenaline and Acetaldehyde", Naunyn-Schmiedeberg's Arch Pharmacol, 300(2): abstract only, 1977.

Bagal et al. "Modulation of Morphine-Induced Antinociception by Ibogaine and Noribogaine", Brain Research, 741(1-2): pp. 258-262, 1996.

Bartlett et al. "The Alkaloids of Tabernanthe iboga. Part IV..sup.1 The Structures of Ibogamine, Ibogaine, Tabernanthine and Voacangine", J. Am. Chem. Soc., 80: pp. 126-136, 1958.

Batrakova. "Pluronic P85 Enhances the Delivery of Digoxin to the Brain: In Vitro and In Vivo Studies", The J. of Pharm. And Exp. Thera, 296, p. 551-557, 2001.

Baumann et al. "Comparative Neurobiology of Ibogaine and its Metabolite, 12-Hydroxyibogaimine (Noribogaine), in Rodents." Conference at New York University, Abstract only, 2000.

Beaubrun. "The Diagnosis and Management of Acute Psychotic Reaction Due to Alcohol and Drugs", Caribb Med J, 36(1): abstract only, 1975.

Beck et al. "Energy-Dependent Reduced Drug Binding as a Mechanism of Vinca Alkaloid Resistance in Human Leukemic Lymphoblasts", Mol Pharmacol, 24(3): abstract only, 1983.

Benet et al. "Pharmacokinetics: Biotransformation of Drugs." In Gilman et al. Goodman and Gilman's the Pharmacological Basis of Therapeutics (1990) :13-16.

Benoist et al. "Comparative Effects of Fagaronine Adriamycin and Aclacinomycin on K562 Cell Sensitivity to Natural-Killer-Mediated Lysis Lack of Agreement Between Alteration of Transferrin Receptor and CD15 Antigen Expressions and Induction of Resistance to Natural Killer", Cancer Immunol Immunother, 30(5): abstract only, 1989.

Bert et al. "Non-Amphetaminic Central Stimulation by Alkaloids from the Ibogaine and Vobasine Series", Planta Med., 54(3): abstract only, 1988.

Bhargava et al. "Effects of ibogaine and noribogaine on the antinociceptive action of mu-, delta- and kappa-opioid receptor agonists in mice", Brain Research 752:234-238, 1997.

Blum et al. "Possible Role of Tetrahydroisoquinoline Alkaloids in Postalcohol Intoxication States", Ann N Y Acad Sci, 273: abstract only, 1976.

Blum et al. "Peyote a Potential Ethnopharmacologic Agent for Alcoholism and Other Drug Dependencies Possible Biochemical Rationale", Clin Toxicol, 11(4): abstract only, 1977.

Blum et al. "Putative Role of Isoquinoline Alkaloids in Alcoholism: A Link to Opiates", Alcohol Clin Exp Res, 2(2): abstract only, 1978.

Brady et al. "Analgesic Effects of Intraventricular Morphine and Enkephalins in Nondependent and Morphine-Dependent Rats", J. Pharmacol. Exp. Ther., 222(1): abstract only, 1982.

Buchi et al. "The total synthesis of iboga alkaloids", J. Am. Chem. Soc. vol. 88, p. 3099-3109, 1966.

Bundgaard. "Design of Prodrugs: Bioreversible Derivatives for Various Functional Groups and Chemical Entities." Design of Prodrugs, 1-10, 1985.

Bussel et al. "Isolated Thrombocytopenia in Patients Infected with HIV Treatment with Intravenous Gamma Globulin", Am J Hematol, 28(2): abstract only, 1988.

Caldwell et al. "The Biochemical Pharmacology of Abused Drugs. III. Cannabis, Opiates, and Synthetic Narcotics", Clin. Pharmacol. Ther., 16:6: abstract only, 1974.

Cankat. "Pharmacological Aspects of Drug Induced Headache", Funct. Neurol., 7:6: abstract only, 1992.

Cappendijk et al. "Inhibitory Effects of Ibogaine on Cocaine Self-Administration in Rats", Eur. J. Pharmacol., 241 (2-3): abstract only, 1993.

Cappendijk et al. "The Inhibitory Effect of Norharman on Morphine Withdrawal Syndrome in Rats: Comparisons with Ibogaine", Behavioural Brain Research, pp. 1-3, 1994.

Castle. "Drugs and Fibrotic Reactions—Part I", Adverse Drug React. Bull., 113: abstract only, 1985.

Chemical abstract, RN 16671-16-2 Registry, 1967.
Chemical abstract, RN 3464-63-9 Registry, 1965.
Chemical abstract, RN 481-87-8 Registry, 1952.
Chemical abstract, RN 4865-78-5 Registry, 1965.
Chemical abstract, RN 53508-36-4 Registry, 1974.
Chemical abstract, RN 57511-56-5 Registry, 1975.
Chemical abstract, RN 77123-15-0 Registry, 1980.
Chemical abstract, RN 83-74-9 Registry, 1934.
Chemical abstract, RN 88660-07-5 Registry, 1983.
Chemical abstract, RN 88660-09-7 Registry, 1983.

Cherny et al. "Opioid responsiveness of cancer pain syndromes caused by neuropathic or nociceptive mechanisms: a combined analysis of controlled, single-dose studies", Neurobiology 44:857-861, 1994.

Cheze et al. "Determination of ibogaine and noribogaine in biological fluids and hair by LC-MS/MS after Tabernanthe iboga abuse", Forensic Science International, Elsevier Scientific Publishers Ireland Ltd, IE, vol. 176. No. 1, pp. 58-66, 2007.

Criel et al. "Drug Dependent Red Cell Antibodies and Intravascular Haemolysis Occurring in Patients Treated with 9 Hydroxy-Methyl-Ellipticinium", Br J Haematol, 46(4): abstract only, 1980.

Damstrup et al. "Retroperitoneal Fibrosis After Long-Term Daily Use of Ergotamine", Int. Urol. Nephrol., 18/3: abstract only, 1986.

Database Registry Chemical Abstracts Service, Columbus, Ohio, US; 1984, "Ibogamine-18-carboxylic acid, 12-methoxy-, potassium sal", Database accession No. 5500-12-9.

(56) References Cited

OTHER PUBLICATIONS

Deecher et al. "Mechanisms of Action of Ibogaine and Harmaline Congeners Based on Radioligand Binding Studies", Brain Research, 571(2): pp. 242-247, 1992.
Diener et al. "Analgesic-Induced Chronic Headache Long-Term Results of Withdrawal Therapy", J Neurol, 236(1): abstract only, 1989.
Dierckx et al. "Intraarterial Sodium Nitroprusside Infusion in the Treatment of Severe Ergotism", Clin. Neuropharmacol., 9/6: abstract only, 1986.
Dzoljic et al. "Effect of Ibogaine on Naloxone-Precipitated Withdrawal Syndrome in Chronic Morphine-Dependent Rats", Arch. Int. Pharmacodyn., 294:64-70, 1988.
Eberwine et al. "Molecular Analysis of Cellular Responses to Opiate Use", Fidia Res. Found. Symp. Ser., 7(Neurotransm. Regul. Gene Transcr.): abstract only, 1991.
Elkind. "Drug Abuse and Headache", Med Clin North Am, 75(3): abstract only, 1991.
Evenson. "Developments in Therapeutic Drug Monitoring and Alkaloid Analysis", Fed Proc, 34(12): abstract only, 1975.
Faglia et al. "Dihydroergocryptine in Management of Microprolactinomas", J Clin Endocrinol Metab, 65(4): abstract only, 1987.
Fairchild et al. "Keynote Address: Multidrug Resistance: A Pleiotropic Response to Cytotoxic Drugs", Int. J. Radiat. Oncol. Biol. Phys., 20/2: abstract only, 1991.
Finkle. "Phencyclidine Identification by Thin-Layer Chromatography. A Rapid Screening Procedure for Emergency Toxicology", Am. J. Clin. Pathol., 70/2: abstract only, 1978.
Fonne-Pfister et al. "Xenobiotic and Endobiotic Inhibitors of Cytochrome P-450db1 Function, the Target of the Debrisoquine / Sparteine Type Polymorphism", Biochem. Pharmacol., 37(20): abstract only, 1988.
Frances et al. "Effects of Ibogaine on Naloxone-Precipitated Withdrawal in Morphine-Dependent Mice", Fundam Clin Pharmacol, 6(8-9): abstract only, 1992.
Gabr et al. "Changes in Absolute Amount of Alkaloids in Datura-Mete) Treated with Certain Growth Regulators", Herba Pot, 21(2): abstract only, 1975.
Garcia et al. "Chronic pain states: pathophysiology and medical therapy", Seminars in Arthritis and Rheumatism, 27:1-16, 1997.
Gennaro. "Remington: The Science and Practice of Pharmacy", Mack Publishing Col., vol. II, pp. 1736 & 1814, 1995.
George et al. "Palliative medicine", Postgrad, Med. Journal, vol. 69, pp. 426-449, 1993.
Gifford et al. "Effect of Chronic Cocaine Treatment on D SUB 2 Receptors Regulating the Release of Dopamine and Acetylcholine in the Nucleus Accumbens and Striatum", Pharmacology, Biochemistry and Behavior, 41(4): abstract only, 1992.
Glick et al. "Effects of Aftereffects of Ibogaine on Morphine Self-Administration in Rats", European Journal of Pharmacology, 195(3): abstract only, 1991.
Glick et al. "Effect of Ibogaine on Acute Signs of Morphine Withdrawal in Rats: Independence from Tremor", Neuropharmacology, 31:5: abstract only, 1992.
Glick et al. "Local Effects of Ibogaine on Extracellular Levels of Dopamine and Its Metabolites in Nucleus Accumbens and Striatum: Interactions with D-Amphetamine", Brain Research, 628(1-2): abstract, 1993.
Glick et al. "Effects of iboga Alkaloids on Morphine and Cocaine Self-Administration in Rats: Relationship to Tremorigenic Effects and to Effects on Dopamine Release in Nucleus Accumbens and Striatum." Brain Research, 657:14-22, 1994.
Glick et al. "Ibogaine-like effects of noribogaine in rats", Brain Research, 713:294-297, 1996.
Gold et al. "Effect of Methadone Dosage on Clonidine Detoxification Efficacy", Am. J. Psychiatry, 137:3: abstract only, 1980.
Gothoni. "Harmine-, Lon-954- and 5-Hydroxytryptophan-Induced Tremors in Rats Withdrawn from Ethanol", Acta Pharmacol Toxicol, 57(1): abstract only, 1985.

Greenwald, et al., "Poly(ethylene glycol) conjugated drugs and prodrugs: a comprehensive review," Crit. Rev. Ther. Drug Carrier Syst., 17(2):101-161, 2000.
Gross. "Effect of Ergot Alkaloids on Serum Prolactin in Non-Psychotic Organic Brain Syndrome of the Elderly", Exp Aging Res, 5(4): abstract only, 1979.
Gunn. "Relations Between Chemical Constitution, Pharmacological Actions, and Therapeutic Uses, in the Harmine Group of Alkaloids", From the Pharmacological Laboratory, University of Oxford:379-396, 1935.
Haber et al. "Tetrahydroisoquinolines—Endogenous Products After Chronic Alcohol Abuse", Pharmazie, 47/1: abstract only, 1992.
Halikas et al. "Treatment of Crack Cocaine Use with Carbamazepine", Am J Drug Alcohol Abuse, 18(1): abstract only, 1992.
Hanks. "Opioid-responsive and opioid-non-responsive pain in cancer", British Medical Bulletin 47:718-731, 1991.
Hardman et al. "Goodman & Gilman's the Parmacological Basis of Therapeutics" (9th ed, 1996) p. 51 and 57-58.
Harsing, Jr. et al. "Evidence that Ibogaine Releases Dopamine from the Cytoplasmic Pool in Isloated Mouse Striatum", Journal of Neural Transmission General Section, 96(3): abstract only, 1994.
Hearn et al. "Identification and Quantitation of Ibogaine and an o-Demethylated Metabolite in Brain and Biological Fluids Using Gas Chromatography-Mass Spectrometry." J. Analytical Toxicology, 19:427-434, 1995.
Heel et al. "Buprenorphine: A Review of Its Pharmacological Properties and Therapeutic Efficacy", Drugs, 17(2): abstract only, 1979.
Henry et al. "Reversible Cerebral Arteriopathy Associated with the Administration of Ergot Derivatives", Cephalalgia, 4/3: abstract only, 1984.
Ho et al. "Metabolism of Harmaline in Rats." Biochemical Pharmacology, 20:1313-1319, 1971.
Hoes. "Clinical Criteria for the Selection of Anxiolytics", Tijdschr. Ther. Geneesm. Onderz., 9/9: abstract only, 1984.
Holbrook. "Nicotine Addiction." In Isselbacher et al. (ed.), "Harrison's Principals of Internal Medicine" 13th Ed., McGraw-Hill Inc., 2433-2437, 1994.
Holzner et al. "The Neuroleptic Sleeping Course in Chronic Headache", Therapiewoche, 35/36: abstract only, 1985.
Huang et al. "Cytotoxicity and Sister Chromatid Exchanges Induced in Vitro by Six Anticancer Drugs Developed in the People's Republic of China", J Natl Cancer Inst, 71(4): abstract only, 1983.
Hubens et al. "Chronic Intake of a Hydrogenated Ergot Alkaloid Causing Peripheral Vascular Ischemia—A Case Report", Vasc. Surg., 21/4: abstract only, 1987.
Isler. "Treatment of Headache", Schweiz. Med. Wochenschr., 114/35: abstract only, 1984.
Jaffe. "Psychopharmacology and Opiate Dependence", U.S. Public Health Serv. Publ., 1957-1967:1836, 1967.
Jaffe. "Drug Addiction and Drug Abuse." In Gilman et al. Goodman and Gilman's The Pharmacological Basis of Therpeutics:522-523, 559-568, 1990.
James. "Linkers for solid phase organic synthesis," Tetrahedron, 55, 1999, pp. 4855-4946.
Jane et al. "High-Performance Liquid Chromatographic Analysis of Basic Drugs on Silica Columns Using Non-Aqueous Ionic Eluents. II. Application of UV, Fluorescence and Electrochemical Oxidation detection", J. Chromatogr., 323(2): abstract only, 1985.
Jansen et al. "Ethnopharmacology of Kratom and the Mitragyna Alkaloids", J Ethnopharmacol, 23(1): abstract only, 1988.
Janzen. "History of Use of Psychotropic Drugs in Central Africa", Psychotropes, 1/2: abstract only, 1983.
Justins. "Management strategies for chronic pain", Annals of the Rheumatic Diseases, vol. 55, pp. 588-596, 1996.
Kalix. "Khat: A Plant with Amphetamine Effects", J Subst Abuse Treat, 5(3): abstract only, 1988.
Kalix. "Pharmacological Properties of the Stimulant Khat", Pharmacol. Ther., 48/3: abstract only, 1990.
Keefner. "A Gas Chromatography-Mass Spectrometry (GCMS) Method for Ibogaine", Society for Neuroscience Abstracts, 19(1-3): abstract only, 1993.

(56) References Cited

OTHER PUBLICATIONS

Keller et al. "Modulation of Neopterin Release by Human Kupffer Cells in Culture: Possible Implication in Clinical Monitoring of HIV-Seropositive Subjects", Cells Hepatic Sinusoid, 3: abstract only, 1991.
Knoll. "Azidomorphines and Homopyrimidazols: A New Approach to the Ideal Analgetic", Acta Physicol Pharmacol Bulg, 3(2): abstract only, 1977.
Knoll. "Azidomorphines: A New Family of Potent Analgesics with Low Dependence Capacity", Prog. Neuro-Psychopharmacol., 3/1-3: abstract only, 1979.
Koch et al. "Drug-Induced Liver Injury in Liver Biopsies of the Years 1981 and 1983, their Prevalence and Type of Presentation", Path. Res. Pract., 179: abstract only, 1985.
Konig. "Psychiatric Intensive Therapy After Acute Alkaloid Withdrawal Syndrome", Infusionsther Klin Ernahr, 6(1): abstract only, 1979.
Kornetsky, "Pharmacology Drugs Affecting Behavior", New York, John Wiley & Sons, pp. 186-187, 1976.
Kostowski et al. "The Effects of Some Hallucinogens on Aggressiveness of Mice and Rats" Pharmacology vol. 7, pp. 259-263, 1972.
Krug. "Cocaine Abuse: Historical, Epidemiologic, and Clinical Perspectives for Pediatricians", Advances in Pediatrics, 36:369-406, 1989.
Kupers et al., "Morphine differentially affects the sensory and affective pain ratings in neuorgenic and idiopathic forms of pain." Pain 47:5-12, 1991.
Lakoski et al. "Electrophysiologic Characterization of an Ibogaine Metabolite in Dorsal Raphe Nucleus and Hippocampus." Soc. Neurosc. 21:716 Abstract only, 1995.
Larson-Prior et al. "Electrophysiologic Characterization of an Ibogaine Metabolite in the Cerebellar Cortex." Soc. Neurosc. 21:716 Abstract only, 1995.
Layer, et al., "Structurally modified ibogaine analogs exhibit differing affinities for NMDA receptors," European Journal of Pharmacology, 1996, 309:159-165.
Lemontt et al. "Increase MDR Gene Expression and Decreased Drug Accumulation in Multidrug-Resistant Human Melanoma Cells", Cancer Res, 48(22): abstract only, 1988.
Leoni et al. "Effect of Cocaine and Morphine on Neutral Endopeptidase Activity of Human Peripheral Blood Mononuclear Cells Cultures with Lectins", Cell Biochem Funct, 11(3): abstract only, 1993.
Lerida et al. "Incidence of Morphine Withdrawal and Quasi-Abstinence Syndrome in a Model of Chronic Pain in the Rat", Neurosci., 81(1-2): abstract only, 1987.
Lewis et al. "Narcotic Analgesics and Antagonists", Annu Rev Pharmacol, 11: abstract only, 1971.
Lewis et al. "Adverse Reactions and Interactions with .beta.-Adrenoceptor Blocking Drugs", Med. Toxicol., 1:5: abstract only, 1986.
Licht et al. "Induction of Multiple-Drug Resistance During Anti-Neoplastic Chemotherapy In-Vitro", Int J Cancer, 49(4): abstract only, 1991.
Ling et al., "Drugs of Abuse-Opiates", in Addtiction Medicine [Special Issue], Western Journal of Medicine, 152:565-572, 1990.
Low et al. "Effects of Acronycine and Cytouchalasin B on the Division of Rat Leukemia Cells", Exp Cell Res, 131(1): abstract only, 1981.
Ma et al. "Inhibition of Respiratory Burst Activity in Alveolar Macrophages by Bisbenzylisoquinoline Alkaloids: Characterization of Drug-Cell Interaction", Exp. Lung Res., 18/6: abstract only, 1992.
Maisonneuve et al. "Interactions of Ibogaine and D-Amphetamine: in vivio Microdialysis and Motor Behavior in Rats." Brain Research 579:87-92, 1992.
Maisonneuve et al. "Interactions Between Ibogaine, a Potential Anti-Addictive Agent, and Morphine: an in Vivo Microdialysis Study", Eur. J. Pharmacol., 199(1): abstract only, 1991.
Maisonneuve et al. "Acute and Prolonged Effects of Ibogaine on Brain Dopamine Metabolism and Morphine-Induced Locomotor Activity in Rats", Brain Research, 575(1): abstract only, 1992.
Martellotta et al. "Effects of the Calcium Antagonist Isradipine on Cocaine Intravenous Self-Administration in Rats", Psychopharmacologia, 113(3-4): Abstract only, 1994.
Martin et al. "Neuropathic Pain in Cancer Patients: Mechanisms, Syndromes, and Clinical Controversies," Journal of Pain and Symptom Management 14(2):99-117, 1997.
Mash et al. "Ligand Binding Profiles of Ibogaine and its O-demethylated Metabolite Noribogaine: Implications for Developing Novel Multi-target Anti-addiction Agents." Soc. Neurosc. (1995) 21:717 Abstract only.
Mash et al, "Properties of Ibogaine and its Principle Metabolite (12-hydroxyibogamine) at the MK-801 binding site of the NMDA receptor complex," Neuroscience Letters, 192, 53-56, 1995.
Mash et al. "Preclinical screening of an ibogaie metabolite (noribogaine) on cocaine-induced hyperlocomotion and cocaine self-administration." Soc. Neurosc. 22:1929 Abstract only, 1996.
Mash et al. "Ibogaine in the Treatment of Heroin Withdrawal," The Alkaloids 56:1-17, 2001.
Mateer et al. "Reversible Ipecac Myopathy", Arch. Neurol., 42/2: abstract only, 1985.
Matharu et al. "Preformulation and Development of Ibogaine Injection for the Treatment of Drug Abuse", Pharmaceutical Research, 10: abstract only, 1993.
Mattingly et al. "Selective Antagonism of Dopamine D Sub1 and D Sub 2 Receptors Does Not Block the Development of Behavioral Sensitization to Cocaine", Psychopharmacologia, 114(2): abstract only, 1994.
McNeish et al. "The 5-HT Sub 3 Antagonist Zacopride Attenuates Cocaine-Induced Increases in Extracellular Dopamine in Rat Nucleus Accumbens", Pharmacology, Biochemistry, and Behavior, 45(4): abstract only, 1993.
Melchior et al. "Preference for Alcohol Evoked by Tetra Hydro Papaveroline Chronically Infused in the Cerebral Ventricle of the Rat", Pharmacol Biochem Behav, 7(1): abstract only, 1977.
Mendelson et al. "Cocaine and Other Commonly Abused Drugs." In Isselbacher et al. Harrison's Principles of Internal Medicine:2429-2433, 1994.
Menzies et al. "Gangrene of the Small Bowel: A Complication of Methysergide Therapy", Aust. N. Z. J. Surg., 52/5: abstract only, 1982.
Metelitsa. "Pharmacological Agents in Controlling Smoking", Biull Vsesoiuznogo Kardiol Nauchn Tsentra, 10(1): abstract only, 1987.
Millan, "k-Opioid Receptors and Analgesia," Trendes in Pharmacologicla Sciences, 11, pp. 70-76, 1990.
Mizuhashi et al. "Antitumor Activities of IKP-104 A 4-1H Pyridizinone Derivative on Cultured and Implanted Tumors", Jpn J Cancer Res, 81(12): abstract only, 1990.
Montefiori et al. "In Vitro Evaluation of Mismatched Double-Stranded RNA (Ampligen) for Combination Therapy in the Treatment of Acquired Immunodeficiency Syndrome", AIDS Res Hum Retroviruses, 5(2): abstract only, 1989.
Mulamba et al., Alcaloides de Tabernanthe Pubescens. Journal of Natural Products, vol. 44, No. 2, p. 184-189, 1981.
Naranjo. "Ibogaine in psychotherapy: psychoanalysis according to Naranjo", part IV, pp. 1-2. http://www.nettuno.it/fiera/electric.italy/bwitif:html, 1969.
Niemann et al, "The Isolation of Rupicoline and Montanine, Two Pseudoindoxyl Alkaloids of Tabernaemontana Rupicola Benth", The Journal of Organic Chemistry, 31(7):2265-2269, 1993.
Nishiyama et al. "Expression of the Multidrug Transporter, P-Glycoproteiin, in Renal and Transitional Cell Carcinomas", Cancer, 71(11):3611-3619, 1993.
Nooter et al. "Multidrug Resistance (MDR) Genes in Haematological Malignancies", Cytotechnology, 12(1-3): abstract only, 1993.
Nunn-Thompson et al. "Pharmacotherapy for Making Cessation", Clin Pharm, 8(10): abstract only, 1989.
Obach et al., "Cythochrome P4502D6 Catalyzes the O-Demethylation of the Psychoactive Alkaloid Ibogaine to 12-Hydroxyibogamine" Drug Metabolism and Disposition 26(8):764-768, 1998.

(56) References Cited

OTHER PUBLICATIONS

O'Hearn et al. "Degenration of Prukinje Cells in Parasagittal Zones of the Cerebellar Vermis After Treatment with Ibogaine of Harmaline", Neuroscience, 55(2): abstract only, 1993.
O'Hearn et al. "Ibogaine Induces Glial Activation in Parasagittal Zones of the Cerebellum", Neuroreport, 4/3: abstract only, 1993.
Pablo et al, "Noribogaine Stimulates Naloxone-Sensitive[35S]GTPgammaS Binding," NeuroReport, 9, pp. 109-114. (Website Publication Date of Dec. 20, 1997.), 1998.
Pacifici et al. "Immunological Effect of Cocaine and Host Resistance in Mice", Int J Immunother, 8(2): abstract only, 1992.
Palyi. "Survivial Responses to New Cytostatic Hexitols of P388 Mouse and K562 Leukemia Cells in Vitro", Cancer Treat. Rep., 70(2): abstract only, 1986.
Pantazis et al. "Efficacy of Camptothecin Congeners in the Treatment of Human Breast Carcinoma Xenografts", Oncology Research, 5(8): abstract only, 1994.
Pehek. "Effects of Cathinone and Amphetamine on the Neurochemistry of Dopamine in Vivo", Neuropharmacology, 29/12: abstract only, 1990.
Perera et al. "Tertiary Indole Alkaloids of *Tabernaemontana dichotoma* Seeds", Planta Med., 49/1: abstract only, 1983.
Perrin. "Clinical Pharmacokinetics of Ergotamine in Migraine and Cluster Headache", Clin. Pharmacokin., 10/4: abstract only, 1985.
Popik et al. "100 Years of Ibogaine: Neurochemical and Pharmacological Actions of a Putative anti-addictive Drug", Pharmacological Reviews 47(2), pp. 235-253, 1995.
Popik et al. "The Putative Anti-Addictive Drug Ibogaine is a Competitive Inhibitor of ( SUP 3 H) Binding to the NMDA Receptor Complex", Psychopharmacologia, 114(4): abstract only, 1994.
Popik et al. "NMDA Antagonist Properties of the pUtative Antiaddictive Drug, Ibogaine", Journal of Pharmaceutical and Experimental Therapeutics, 275(2), 753-760, 1995.
Pulvirenti et al. "Lisuride Reduces Intravenous Cocaine Self-Administration in Rats", Pharmacology, Biochemistry and Behavior, 47(4): abstract only, 1994.
Qiu et al. "The Influence of Chronic Nicotine Treatment on Stress-Induces Gastric Ulceration and Emptying Rate in Rats", Experientia, 48(4): abstract only, 1992.
Radouco-Thomas, et al. "Adverse effects to Psychotomimetics. Proposition of a Psychopharmacological Classification." Pharmacologie, Toxicologie, et abus des psychotomimetiques (hallucinogens), 109, 1974, abstract only.
Rezvani et al. "Noribogaine, a Primary Ibogaine Metabolite, Reduces Alcohol Intake in P and Fawn-Hooded Rats." RSA Annual Scientific Meeting Abstract only, 1995.
Rezvani et al. "Reduction of Alcohol Intake in Alcohol Preferring Fawn-hooded and P Rats by Noribogaine, the Primary Metabolite of Ibogaine." NIDA Monograph Series (1996) 162:281 Abstract only.
Ricceri et al. "Postnatal cocaine Esposure Affects Neonatal Passive Avoidance Performance and Cholinergic Development in Rats", Pharmacology, Biochemistry and Behavior, 45(2): abstract only, 1993.
Rodriguez et al. "Cocaine Adminstration Prior to Reactivation Facilitates Later Acquisition of an Avoidance Response in Rats", Psychopharmacologia, 112(2-3): abstract only, 1993.
Rosenmund et al. "Ibogamin, Ibogain and Epiibogamin" Chem. Ber. vol. 108, p. 1871-1895, 1975. structures and abstract only.
Sachs et al. "Corneal Complications Associated with the Use of Crack Cocaine", Ophthalmology, 100(2): abstract only, 1993.
Salmoiraghi et al. "Effects of LSD 25, BOL 148, Bufotenine, Mescaline and Ibogaine on the Potentiation of Hexobarbital Hypnosis Produced by Serotonin and Reserpine." J. Pharm and Exp Ther. vol. 120. No. 1, pp. 20-25, 1957.
Samadi-Baboli et al. "Preparation of Low Density Lipoprotein-9-Methoxy-Illipticin Complex and Its Cytotoxic Effect Against L1210 and P 388 Leukemic Cells in Vitro", Eur J Cancer Clin Oncol, 25(2): abstract only, 1989.
Saper et al. "Ergotamine Tartrate Dependency: Features and Possible Mechanisms", Clin. Neuropharmacol., 9/3: abstract only, 1986.

Schecter et al. "Comparison of the Behavioral Effects of Ibogaine from Three Sources: Mediation of Discriminative Activity", European Jornal of Pharmacology, 249(1): abstract only, 1993.
Schneider et al., "Potentiation Action of Ibogaine on Morphine Analgesia" Experiential vol. 12, pp. 323-324, 1956.
Schneider et al. "Analysis of the Cardiovascular Action of Ibogaine Hydrochloride (1)" Arch. Int. Pharmacodyn. vol. 110, pp. 92-102, 1957.
Schneider et al., Neuropharmacological Studies of Ibogaine: An Indole Alkaloid with Central Stimulant Properties Ann. of N.Y. Acad. Sci. vol. 66, pp. 765-776, 1957.
Schnider et al. "Use and Abuse of Analgesics in Tension-Type Headache", Cephalalgia, 14/2: abstract only, 1994.
Schuckit. "Alcohol and Alcoholism." In Isselbacher et al. Harrison's Principles of Internal Medicine :2420-2425, 1994.
Schuckit et al. "Opioid Drug Use." In Isselbacher et al. Harrison's Principles of Internal Medicine :2425-2429, 1994.
Seeber et al. "In Vivo Resistance Towards Anthracyclines, Etoposide, and Cis-Diamminedichloroplatinum (II)", Cancer Res., 42(11): abstract only, 1982.
Sehested et al. "The Carboxylic Ionophore Monensin Inhibits Active Drug Efflux and Modulates In-Vitro Resistance in Daunorubicin Resistant Enrlich Ascites Tumor Cells", Biochem Pharmacol, 37(17): abstract only, 1988.
Sershen et al. "Ibogaine Antagonizes Cocaine-Induced Locomotor Stimulation in Mice", Life Sci., 50(15): abstract only, 1992.
Sershen et al. "Ibogaine Reduces Amphetamine-Induced Locomotor Stimulation in C57BL/6By Mice, but Stimulates Locomotor Activity in Rats", Life Sci., 51(13): abstract only, 1992.
Sershen et al. "Ibogaine Reduces Preference for Cocaine Consumption in C57BL/6By Mice", Pharmacol., Biochem. Behay., 47(1): abstract only, 1994.
Shen et al. "Antagonists at Excitatory Opioid Receptors on Sensory Neurons in Culture Increase Potency and Specificity of Opiate Analgesics and Attenuate Development of Tolerance / Dependence", Brain Research, 636(2): abstract only, 1994.
Sheppard. "A Preliminary Investigation of Ibogaine: Case Reports and Recommendations for Further Study", J. Subst. Abuse Treat., 11/4: abstract only, 1994.
Shir et al., "Neuropathic pain unrelieved by morphine, alleviated by haloperidol" Harefuah 118(8):452-454, Abstract only, 1990.
Shook et al. "A cyclic Somatostatin Analog that Precipitates Withdrawal in Morphine-Dependent Mice", NIDA Res. Monogr., 76(Probl. Drug Depend.): abstract only, 1987.
Sinkula et al. "Rationale for Design for Biologically Reversible Drug Derivatives: Prodrugs." Journal of Pharmaceutical Sciences, 64(2):181-210, 1975.
Slotkin et al. "A Model of Harmine Metabolism in the Rat." The Journal of Pharmacology and Experimental Therapeutics, 174(3):456-462, 1970.
Slotkin et al. "Blood Levels and Urinary Excretion of Harmine and its Metabolites in Man and Rats." The Journal of Pharmacology and Experimental Therapeutics, 173(1):26-30, 1970.
Slotkin et al. "Urinary Metabolites of Harmine in the Rat and their Inhibition of Monoamine Oxidase." Biochemical Pharmacology 19:125-131, 1970.
Sloviter et al. "A Common Mechanism of Lysergic Acid, Indolealkylamine and Phenethylamine Hallucinogens: Serotonergic Mediation of Behavioral Effects in Rats" J. Pharm. Exp. Ther. vol. 214, No. 2, pp. 231-238, 1980.
Smith. "Interaction of Biogenic Amines with Ethanol", Adv Exp Med Biol, 56: abstract only, 1975.
Snyder, et al., "Practical HPLC Method Development", 1997, 2nd Ed., pp. 214-218, 266, 267, 282 & 283, John Wiley & Sons, Inc.
Solinas et al. "Solid-supported reagents and catch-and-release techniques in organic synthesis". Synthesis Aug. 16, 2007 DE LNKD-DOI:10.1055/S-2007-983806, No. 16., pp. 2409-2453, 2007.
Stahl, et al., "Handbook of Pharmaceutical Salts", 1998, p. 250 John Wiley & Sons.
Stella. "Pro-drugs: An Overview and Definition." Prodrugs As Novel Drug Delivery System. ACS Symposium Series :1-115, 1975.
Stella. "Pro-drugs as Novel Drug Delivery Systems", Higuchi, T. et al., ed. (American Chemical Society, Washington), pp. 1-49, 1975.

(56) References Cited

OTHER PUBLICATIONS

Sugiyama et al. "Quantitative Analysis of Cell-Kill Effects of Anticancer Drugs: Consideration of Both In Vitro and In Vivo Expreimental Systems", Gan to Kagaku Ryoho, 14(12): abstract only, 1987.
Tarnower et al. "Ergotism Masquerading as Arteritis", Postgrad Med, 85(1): abstract only, 1989.
Teoh et al. "Buprenorphine Effects on Morphine- and Cocaine-Induced Subjective Responses by Drug—Dependent Men", Journal of Clinical Psychopharmacology, 14(1): abstract only, 1994.
Tfelt-Hansen et al. "Nitroglycerin for Ergotism. Experimental Studies in Vitro and in Migraine Patients and Treatment of an Overt Case", Eur. J. Clin. Pharmacol., 22/2: abstract only, 1982.
Torrenegra et al. "Alkaloids of stemmadenia grandiflora", Phytochemistry, 27(6): pp. 1843-1848, 1988.
Tsuruo. "Multidrug Resistance: A Transport System of Antitumor Agents and Xenobiotics", Princess Takamatsu Symp, 21: abstract only, 1990.
Uldry et al. "Cerebrovascular Accidents in Relation to Drug Consumption or Drug Abuse", Schweiz Rundsch Med Prax, 78(23): abstract only, 1989.
Valadez et al. "Persistence of the Ability of Amphetamine Preexposure to Facilitate Acquistion of Cocaine Self-Administration", Pharmacology, Biochemistry and Behavior, 47(1): abstract only, 1994.
Valencia et al. "Obovatine, a new bisindole alkaloid from stemmadenia obovata", Journal of Natural Products, 58(1):pp. 134-137, 1995.
Vescovi et al. "Successful Treatment of Opiate Withdrawal Using Lysine Acetylsalicylate", Curr. Ther. Res., Clin. Exp., 33/5: abstract only, 1983.
Villalba et al. "Uses and Abuses of Ipecacuana Syrup", Farm. Clin., 9/1: abstract only, 1992.
Wells et al. "Recognition and Treatment of Arterial Insufficiency from Cafergot", J. Vasc. Surg., 4/1: abstract only, 1986.
Whitaker et al. "High Affinity 3H-Serotonin Binding to Caudate: Inhibition by Hallucinogenic and Serotonergic Drugs", Psychopharmacology, vol. 59, pp. 1-5, 1978.
Whitaker et al., "Selective Labeling of Serotonin Receptors by d'(3H)Lysergic Acid Diethylamide in Calf Caudate", Proc. Natl. Acad. Sci., USA vol. 75, No. 12, pp. 5783-87, 1978.
Whittaker et al. "Recurrent Laryngeal Nerve Paralysis in Patients Receiving Vincristine and Vinblastine", Br Med J, 1(6071): abstract only, 1977.
Widler et al. "Pharmacodynamics and Pharmacokinetics of Khat: a Controlled Study", Clin. Pharmacol. Ther., 55/5: abstract only, 1994.
Wildmann. "Heterocycles as Physiological Ligands for the Benzodiazepine Receptor and for Other Binding Sites", Pharmacol Res, 21(6): abstract only, 1989.
Williams, Jr. et al. "The 'Alice in Wonderland' Experience Ergot Alkaloid Therapy for Prolactin-Secreting Pituitary Tumors", West. J. Med., 138/3: abstract only, 1983.
Wishart et al. "Is Multidrug Resistance Relevant in Breast Cancer", Eur. J. Surg. Oncol., 17/5: abstract only, 1991.
Witt et al. "Pharmacodynamic and Pharmacokinetic Characterization of Poly(Ethylene glycol) Conjugation to Met-Enkephalin Analog [$_D$-Pen$^2$,$_D$-Pen$^5$]-enkephalin (DPDPE)", J. of Pharm. and Exp. Thera., 298(2), pp. 848-856, 2001.
Witt et al. "Pluronic P85 Block Copolymer Enhances Opioid Pepetide Analgesia", J. of Pharm. and Exp. Thera., 303(2), pp. 760-767, 2002.
Worz. "Effects and Risks of Psychotropic and Analgesic Combinations", Am. J. Med., 75/5A: abstract only, 1983.
Yang, et al., "Prodrug based optimal drug delivery via membrane transporter/receptor," Expert. Opin. Biol. Ther., 1(2):159-175, 2001.
Zetler et al. "Cerebral Pharmacokinetics of Tremor-Producing Harmala and Iboga Alkaloids" Pharmacology vol. 7, No. 4, pp. 237-248, 1972.
D220 Zetler et al. "Pharmacokinetics in the Rat of the Hallucinogenic Alkaloids Harmine and Harmaline." Naunyn-Schmiedeberg's Arch. Pharmacol., 285, 273-292, 1974.

* cited by examiner

PHOSPHATE ESTERS OF NORIBOGAINE

CROSS-REFERENCE TO RELATED APPLICATION

This application claims the benefit under 35 U.S.C. §119 (e) of U.S. Provisional Application No. 61/569,150, filed Dec. 9, 2011, which is incorporated herein by reference in its entirety.

FIELD OF THE INVENTION

This invention is directed to phosphate esters of noribogaine.

STATE OF THE ART

Noribogaine is a metabolite of ibogaine and is sometimes referred to as 12-hydroxyibogaine. U.S. Pat. No. 2,813,873 claims noribogaine albeit as "12-O-demethylibogaine" while providing an incorrect structural formula for ibogaine. Noribogaine can be depicted by the following formula:

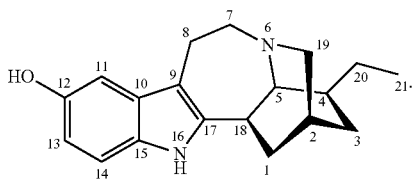

Noribogaine and its pharmaceutically acceptable salts have recently received significant attention as a non-addictive alkaloid useful in treating drug dependency (U.S. Pat. No. 6,348,456) and as a potent analgesic (U.S. Pat. No. 7,220,737).

Noribogaine is typically administered orally or intravenously and becomes systemically available to the treated patient.

SUMMARY OF THE INVENTION

This invention is directed in part to phosphate esters of noribogaine and a vicinal dihydro derivative of noribogaine and compositions thereof. The phosphate esters of this invention can be a mono-, di-, or a tri-phosphate or salts thereof. Accordingly, in certain aspects, the phosphate esters of the invention are represented by a compound of Formula I:

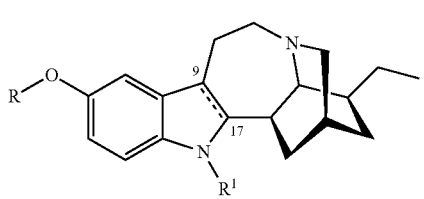

wherein:

⌿⌿ refers to a single or a double bond provided that when

⌿⌿ is a single bond, Formula I refers to the corresponding 9,17 vicinal dihydro compound;

R is selected from the group consisting of hydrogen, a monophosphate, a diphosphate and a triphosphate; and $R^1$ is hydrogen, a monophosphate, a diphosphate or a triphosphate;

provided that at least one of R and $R^1$ is not hydrogen;

wherein one or more of the monophosphate, diphosphate and triphosphate groups of R and $R^1$ may be an ester, preferably a $C_1$-$C_6$ ester, or a salt thereof.

This invention is also directed to dihydronoibogaine derivative of Formula II:

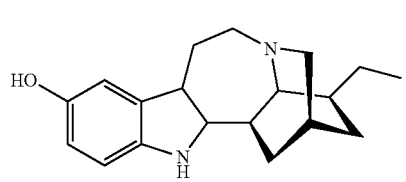

or pharmaceutically acceptable salts thereof and pharmaceutical compositions and therapeutic uses thereof. It is contemplated that the compound of Formula II is oxidized back to noribogaine under relatively mild oxidation conditions, such as those existing in vivo and can act as a metered source of noribogaine, particularly, in vivo.

As used herein, the 9,17 dihydro noribogaine and phosphate ester derivatives thereof include the 9α, 17β; 9α, 17α; 9β, 17α; and 9β, 17β stereoisomers.

In one of its composition aspects, this invention provides for a pharmaceutical composition comprising a therapeutically effective amount of a compound of Formula I or II above and at least a pharmaceutically acceptable excipient.

In one of its method aspects, this invention is directed to a method for treating pain in a patient, which method comprises administering to said patient with a therapeutically effective amount of a compound of Formula I or II above optionally in the presence of at least a pharmaceutically acceptable excipient.

In another of its method aspects, this invention is directed to a method for treating addiction in a patient which method comprises administering to said patient a therapeutically effective amount of a compound of Formula I or II above optionally in the presence of at least a pharmaceutically acceptable excipient.

DETAILED DESCRIPTION OF THE INVENTION

It is to be understood that this invention is not limited to particular embodiments described, as such may, of course, vary. It is also to be understood that the terminology used herein is for the purpose of describing particular embodiments only, and is not intended to be limiting, since the scope of this invention will be limited only by the appended claims.

It must be noted that as used herein and in the appended claims, the singular forms "a", "an", and "the" include plural referents unless the context clearly dictates otherwise. Thus, for example, reference to "a compound of Formula I" includes a plurality of compounds of Formula I such as a mixture of two or more of such compounds.

Definitions

Unless defined otherwise, all technical and scientific terms used herein have the same meaning as commonly understood by one of ordinary skill in the art to which this invention belongs. As used herein, the following terms have the following meanings.

As used herein, the term "comprising" or "comprises" shall mean that the compositions and methods include the recited elements, but not excluding others. "Consisting essentially of" when used to define compositions and methods, shall mean excluding other elements of any essential significance to the combination for the stated purpose. Thus, a composition or method consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention.

The term "about" when used before a numerical designation, e.g., temperature, time, amount, and concentration, including range, indicates approximations which may vary by (+) or (−) 10%, 5% or 1%.

As stated above, the invention is directed in part to a phosphate ester of noribogaine and dihydronoribogaine, esters thereof, or pharmaceutically acceptable salts of each thereof.

As used herein, the term "noribogaine" refers to the compound:

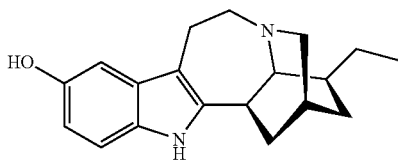

as well as its pharmaceutically acceptable salts thereof. Conventionally, noribogaine is prepared by demethylation of naturally occurring ibogaine:

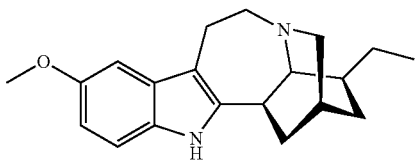

which is isolated from *Tabernanthe iboga*, a shrub of West Africa. Demethylation may be accomplished by conventional techniques such as by reaction with boron tribromide/methylene chloride at room temperature followed by conventional purification. (See, for example, Huffman, et al., J. Org. Chem. 50:1460 (1985). This invention is not limited to any particular chemical form of noribogaine and the drug may be given to patients either as a free base or as a pharmaceutically acceptable addition salt.

As used herein, the term "phosphate ester" refers to any one of the mono-, di- or triphosphate esters of noribogaine, wherein the mono-, di- or triphosphate ester moiety is bonded to the 12-hydroxy group and/or the indole nitrogen of noribogaine.

As used herein, the term "monophosphate" refers to the group —P(O)(OH)$_2$.

As used herein, the term "diphosphate" refers to the group —P(O)(OH)—OP(O)(OH)$_2$.

As used herein, the term "triphosphate" refers to the group —P(O)(OH)—(OP(O)(OH))$_2$OH.

As used herein, the term "ester" as it refers to esters of the mono-, di- or triphosphate group means esters of the monophosphate can be represented by the formula —P(O)(OR$^2$)$_2$, where each R$^2$ is independently hydrogen, C$_1$-C$_{12}$ alkyl, C$_3$-C$_{10}$ cycloalkyl, C$_6$-C$_{14}$ aryl, heteroaryl of 1 to 10 carbon atoms and 1 to 4 optionally oxidized heteroatoms selected from the group consisting of oxygen, nitrogen, and sulfur and the like, provided that at least one R$^2$ is not hydrogen. Likewise, exemplary esters of the di- or triphosphate can be represented by the formulas —P(O)(OR$^2$)—OP(O)(OR$^2$)$_2$ and —P(O)(OR$^2$)—(OP(O)(OR$^2$))$_2$OR$^2$, where R$^2$ is as defined above.

As used herein, the term "alkyl" refers to alkyl groups having from 1 to 12 carbon atoms, preferably 1 to 6 carbon atoms and more preferably 1 to 3 carbon atoms. The alkyl group may contain linear or branched carbon chains. This term is exemplified by groups such as methyl, ethyl, n-propyl, iso-propyl, n-butyl, t-butyl, n-pentyl and the like. The term "C$_x$ alkyl" refers to an alkyl group having x carbon atoms, wherein x is an integer, for example, C$_3$ refers to an alkyl group having 3 carbon atoms.

As used herein, the term "cycloalkyl" refers to cyclic hydrocarbyl groups of from 3 to 10 carbon atoms having single or multiple cyclic rings including, by way of example, adamantyl, cyclopropyl, cyclobutyl, cyclopentyl, cyclooctyl and the like.

As used herein, the term "aryl" refers to an aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, and the like) provided that the point of attachment is at an aromatic carbon atom.

As used herein, the term "heteroaryl" refers to an aromatic group of from 1 to 10 carbon atoms and 1 to 4 heteroatoms selected from the group consisting of oxygen, nitrogen, sulfur within the ring, wherein the nitrogen and/or sulfur atom(s) of the heteroaryl are optionally oxidized (e.g., N-oxide, —S(O)— or —S(O)$_2$—). Such heteroaryl groups can have a single ring (e.g., pyridyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. Examples of heteroaryls include pyridyl, pyrrolyl, indolyl, thiophenyl, and furyl.

As used herein, the terms "stress" or "anxiety" refer to the consequence when a patient fails to respond appropriately to emotional or physical threats, which may be actual or imagined. Stress symptoms or conditions may be cognitive, emotional, physical or behavioral, including, but not limited to a state of alarm and adrenaline production, short-term resistance as a coping mechanism, exhaustion, irritability, muscular tension, inability to concentrate, poor judgment, a general negative outlook, excessive worrying, moodiness, irritability, agitation, inability to relax, feeling lonely, isolated or depressed, aches and pains, diarrhea or constipation, nausea, dizziness, chest pain, headache, rapid heartbeat, eating too much or not enough, sleeping too much or not enough, social withdrawal, procrastination or neglect of responsibilities, increased alcohol, nicotine or drug consumption, and nervous habits such as pacing about or nail-biting. Stress can develop into a disabling disorder of excessive and irrational fears, such as obsessive-compulsive disorder, panic disorder, acute stress disorder and post traumatic stress disorder (PTSD).

As used herein, the term "protecting group" or "Pg" refers to well known functional groups which, when bound to a functional group, render the resulting protected functional group inert to the reaction to be conducted on other portions of the compound and the corresponding reaction condition, and which can be reacted to regenerate the original functionality under deprotection conditions. The identity of the protecting group is not critical and is selected to be compatible with the remainder of the molecule. In one embodiment, the protecting group is an "amino protecting group" which protects the amino functionality of noribogaine or derivatives thereof during the synthesis described here. Examples of amino protecting groups include, for instance, benzyl, acetyl, oxyacetyl, carbonyloxybenzyl (Cbz), and the like. In another embodiment, the protecting group is a "hydroxy protecting group" which protects the hydroxyl functionality of noribogaine or a derivative thereof during the synthesis described here. Examples of hydroxyl protecting groups include, for instance, benzyl, p-methoxybenzyl, p-nitrobenzyl, allyl, trityl, dialkylsilylethers, such as dimethylsilyl ether, and trialkylsilyl ethers such as trimethylsilyl ether, triethylsilyl ether, and t-butyldimethylsilyl ether; esters such as benzoyl, acetyl, phenylacetyl, formyl, mono-, di-, and trihaloacetyl such as chloroacetyl, dichloroacetyl, trichloroacetyl, trifluoroacetyl; and carbonates such as methyl, ethyl, 2,2,2-trichloroethyl, allyl, and benzyl. Additional examples of amino and hydroxy protecting groups are found in standard reference works such as Greene and Wuts, Protective Groups in Organic Synthesis., 2d Ed., 1991, John Wiley & Sons, and McOmie Protective Groups in Organic Chemistry, 1975, Plenum Press. Methods for protecting and deprotecting the phenolic hydroxyl and indole N—H groups disclosed herein can be found in the art, and specifically in Greene and Wuts, supra, and the references cited therein.

As used herein, the term "pharmaceutically acceptable salt" refers to salts derived from organic or inorganic acids. Examples of such acids include, without limitation, hydrochloric acid, hydrobromic acid, phosphoric acid, sulfuric acid, methane sulfonic acid, phosphorous acid, nitric acid, perchloric acid, acetic acid, tartaric acid, lactic acid, succinic acid, citric acid, malic acid, maleic acid, aconitic acid, salicylic acid, thalic acid, embonic acid, enanthic acid, and the like. It is understood that the salt of the compound of Formula I above can be of either the phosphate, diphosphate or triphosphate or of an ester thereof.

As used herein, the term "therapeutically acceptable amount" refers to the amount of a composition of this invention that is sufficient to effect treatment, as defined herein, when administered to a subject in need of such treatment. The therapeutically effective amount will vary depending upon the subject and condition being treated, the weight and age of the subject, the severity of the condition, the particular composition or excipient chosen, the dosing regimen to be followed, timing of administration, the manner of administration and the like, all of which can be determined readily by one of ordinary skill in the art.

As used herein, the term "treatment" or "treating" means any treatment of a disease or condition in a patient, including:
  preventing or protecting against the disease or condition, that is, causing the clinical symptoms not to develop, for example, in a subject at risk of suffering from such a disease or condition, thereby substantially averting onset of the disease or condition;
  inhibiting the disease or condition, that is, arresting or suppressing the development of clinical symptoms; and/or
  relieving the disease or condition, that is, causing the regression of clinical symptoms.

As used herein, the term "pain" refers to all types of pain, including neuropathic and nociceptive pain. It is also contemplated that the compositions disclosed herein can be used to treat other types of pain such as phantom pain which is the sensation of pain from a limb or organ that has been lost or from which a person no longer receives physical signals, and is an experience almost universally reported by amputees and quadriplegics.

As used herein, the term "addiction" refers to a persistent behavioral pattern marked by physical and/or psychological dependency to a substance, particularly drugs such as narcotics, stimulants, and sedatives, including but not limited to heroin, cocaine, alcohol, nicotine, caffeine, amphetamine, desoxyephedrine, methadone and combinations thereof. As used herein, the "treatment of addiction in a patient" refers to reducing the withdrawal symptoms associated with drug dependency as well as alleviating drug cravings in addicts. Such symptoms include nausea, vomiting, anxiety, abdominal cramps, muscle pain, chills and headache.

As used herein, the term "patient" or a "subject" refers to mammals and includes humans and non-human mammals.

Compounds of the Invention

In one aspect of this invention is provided a compound of Formula I:

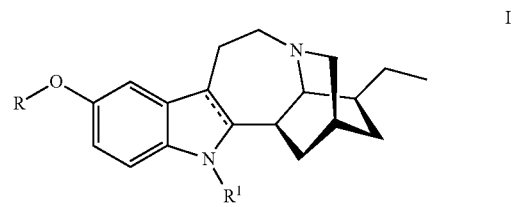

wherein:

⚏ refers to a single or a double bond provided that when

⚏ is a single bond, Formula I refers to the corresponding vicinal dihydro compound;

R is selected from the group consisting of hydrogen, a monophosphate, a diphosphate and a triphosphate; and $R^1$ is hydrogen, a monophosphate, a diphosphate or a triphosphate;

provided that at least one of R and $R^1$ is not hydrogen;

wherein one or more of the monophosphate, diphosphate and triphosphate groups of R and $R^1$ may be an ester, preferably a $C_1$-$C_6$ alkyl ester, or a salt of each thereof.

In some embodiments, ⚏ refers to a double bond. In some embodiments, ⚏ refers to a single bond.

In some embodiments, R is a monophosphate. In some embodiments, R is a diphosphate. In some embodiments, R is a triphosphate. In some embodiments, R is hydrogen.

In some embodiments, $R^1$ is hydrogen. In some embodiments, $R^1$ is a monophosphate. In some embodiments, $R^1$ is a diphosphate. In some embodiments, $R^1$ is a triphosphate.

In some embodiments, R is a monophosphate and $R^1$ is hydrogen. In some embodiments, R is a diphosphate and $R^1$ is hydrogen. In some embodiments, R is a triphosphate and $R^1$ is hydrogen.

In some embodiments, R is hydrogen or a monophosphate and $R^1$ is monophosphate. In some embodiments, R is hydrogen or a diphosphate and $R^1$ is monophosphate. In some embodiments, R is hydrogen or a triphosphate and $R^1$ is monophosphate.

In some embodiments, R is a hydrogen or monophosphate and $R^1$ is diphosphate. In some embodiments, R is a hydrogen or diphosphate and $R^1$ is diphosphate. In some embodiments, R is hydrogen or a triphosphate and $R^1$ is diphosphate.

In some embodiments, R is hydrogen or a monophosphate and $R^1$ is triphosphate. In some embodiments, R is hydrogen or a diphosphate and $R^1$ is triphosphate. In some embodiments, R is hydrogen or a triphosphate and $R^1$ is triphosphate.

In one embodiment, the compound of Formula I is a compound of Formula I-A:

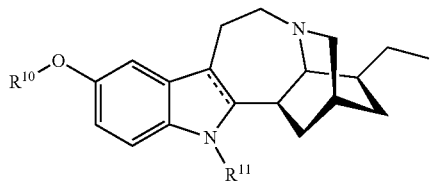

I-A wherein:

⚡ refers to a single or a double bond provided that when ⚡ is a single bond, Formula I-A refers to the corresponding vicinal dihydro compound;

$R^{10}$ is hydrogen or

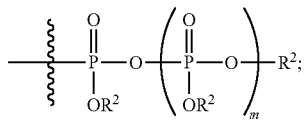

$R^{11}$ is hydrogen or

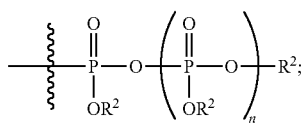

provided that both $R^{10}$ and $R^{11}$ are not hydrogen;
each m independently is 0, 1, or 2;
each n independently is 0, 1, or 2;
each $R^2$ is independently hydrogen, $C_1$-$C_{12}$ alkyl, $C_3$-$C_{10}$ cycloalkyl, $C_6$-$C_{14}$ aryl, heteroaryl of 1 to 10 carbon atoms and 1 to 4 optionally oxidized heteroatoms selected from the group consisting of oxygen, nitrogen, and sulfur;
or a salt thereof.

In some embodiments, ⚡ refers to a double bond. In some embodiments, ⚡ refers to a single bond.

In some embodiments, $R^{10}$ is hydrogen. In some embodiments, $R^{11}$ is:

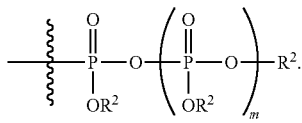

In some embodiments, $R^{11}$ is hydrogen. In some embodiments, $R^{11}$ is:

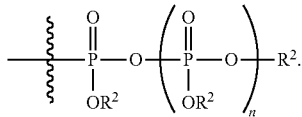

In some embodiments, m is 0. In some embodiments, m is 1. In some embodiments, m is 2. In some embodiments, n is 0. In some embodiments, n is 1. In some embodiments, n is 2.

In some embodiments, each $R^2$ is independently selected from hydrogen or $C_1$-$C_6$ alkyl. In some embodiments, $R^2$ is hydrogen.

In a preferred embodiment, this invention provides compounds of Formula I-A as tabulated below and pharmaceutically acceptable salts thereof.

| Comp. # | $R^{10}$ | m | $R^{11}$ | n | ⚡ | $R^2$ |
|---|---|---|---|---|---|---|
| i | ![phosphate group]  | 0 | hydrogen | — | double bond | hydrogen |
| ii | ![phosphate group] | 1 | hydrogen | — | double bond | hydrogen |
| iii | ![phosphate group] | 2 | hydrogen | — | double bond | hydrogen |
| iv | ![phosphate group] | 0 | hydrogen | — | single bond | hydrogen |

-continued
| Comp. # | $R^{10}$ | m | $R^{11}$ | n | ⌇ | $R^2$ |
|---|---|---|---|---|---|---|
| v | | 1 | hydrogen | — | single bond | hydrogen |
| vi | | 2 | hydrogen | — | single bond | hydrogen |
| vii | hydrogen | — | | 0 | double bond | hydrogen |
| viii | hydrogen | — | | 1 | double bond | hydrogen |
| ix | hydrogen | — | | 2 | double bond | hydrogen |
| x | hydrogen | — | | 0 | single bond | hydrogen |
| xi | hydrogen | — | | 1 | single bond | hydrogen |
| xii | hydrogen | — | | 2 | single bond | hydrogen |
| xiii | | 0 | | 0 | double bond | hydrogen |
| xiv | | 0 | | 0 | single bond | hydrogen |

In another of its compound aspects, this invention provides a dihydronoribogaine derivative of Formula II:

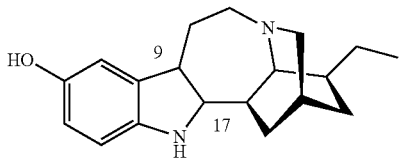

and pharmaceutically acceptable salts thereof. As used herein, the 9,17 dihydro noribogaine and phosphate ester derivatives thereof include the 9α, 17α; 9α, 17β; 9β, 17α; and 9β, 17β stereoisomers. In one embodiment, the steroisomer is 9α, 17α stereoisomer.

Methods of the Invention

Noribogaine has properties that are well suited to the treatment of pain and of withdrawal symptoms associated with drug dependency or abuse. In particular, it has been discovered that noribogaine binds to at least two classes of opioid receptors that have been associated with pain relief, the μ and κ receptors. In the case of the μ-type receptors, noribogaine acts as an opiate agonist. In addition, noribogaine elevates brain serotonin levels by blocking synaptic reuptake. It is believed that such levels (as well as ligand interactions at the μ and κ opiate receptors) play a role in the anxiety and drug cravings experienced by addicts during withdrawal. Noribogain is the first μ opioid agonist which demonstrates analgesic properties without the propensity to cause addiction.

A noribogaine phosphate of Formula I is a novel compound wherein the 12-hydroxyl group and/or the indole N—H of noribogaine is replaced with a biocompatible phosphate group. This group, including esters and/or salts thereof, exhibit enhanced solubility over noribogaine. In addition, the phosphate group will hydrolyze in the gastrointestinal tract in a manner which provides for a titrated release of noribogaine. The dihydronoribogaine of Formula II is contemplated to be oxidized, over time, for example under aerobic conditions existing in vivo, to noribogaine. As noribogaine has shown the potential for rapid absorption in the stomach, a titrated release of noribogaine in accordance with this invention is important in controlling the amount of noribogaine absorbed by the body over a unit period of time.

Treatment of Pain

Another aspect of this invention is directed to a method for treating pain in a patient. The pain can be any type of pain including, but not limited to neuropathic or nociceptive pain, and various types thereof including somatic, visceral and phantom pain. Accordingly, in one embodiment, the method comprises administering to said patient a pharmaceutical composition comprising a therapeutically effective amount of a compound of Formula I. See, for example, U.S. Pat. No. 7,220,737 (incorporated herein in its entirety by reference).

Treatment of Addiction

Noribogaine has been known to be used to treat patients for alleviating the symptoms associated with withdrawal from drug dependency. Accordingly, this invention is also directed to a method for treating addiction in a patient, which method comprises administering to said patient a pharmaceutical composition comprising a therapeutically effective amount of a compound of Formula I. See, for example, U.S. Pat. No. 6,348,456 (incorporated herein in its entirety by reference).

In certain embodiments, the treatment of addiction in a patient comprises alleviating the symptoms associated with withdrawal from drug dependency. Such symptoms include nausea, vomiting, anxiety, abdominal cramps, muscle pain, chills and headache. In addition, noribogaine treatment decreases the drug cravings normally experienced by addicts after cessation of the self administration of the abused substance. It is contemplated that the compositions disclosed herein comprising a compound of Formula I are especially useful in the treatment of addiction to narcotics such as heroin and methadone. However, it is also useful in treating patients addicted to cocaine, alcohol, amphetamines and combinations of these drugs.

Treatment of Stress

Stress can develop into a disabling disorder of excessive and irrational fears, such as obsessive-compulsive disorder, panic disorder, acute stress disorder and post traumatic stress disorder (PTSD). PTSD is a severe stress disorder that can develop after exposure to an event which results in psychological trauma. Such events usually involve death of someone else, threat of death to oneself or to someone else, or trauma to the physical, sexual, or psychological integrity of one's own or someone else. PTSD may be an acute stress response or a long term stress response to such an event when it overwhelms one's ability to cope. Symptoms of PTSD include some or all of the following: recurrent re-experiencing of the trauma, for example, intrusive, upsetting memories of the event, flashbacks of the traumatic events (acting or feeling like the event is happening again), recurring nightmares (either of the event or of other frightening things); feelings of intense distress and/or intense physical reactions when reminded of the trauma; avoidance to the point of having a phobia of places, people, and experiences that remind the sufferer of the trauma and a general numbing of emotional responsiveness; inability to remember important aspects of the trauma; and physical signs of hyperarousal, including sleep problems, trouble concentrating, irritability, anger, poor concentration, blackouts or difficulty remembering things, increased tendency and reaction to being startled, and hypervigilance to threat. Other symptoms include anhedonia, lack of interest in activities that used to be enjoyed, emotional deadness, distancing oneself from people, and/or a sense of a limited future (for example, not being able to think about the future or make future plans, not believing one will live much longer), guilt, shame, self-blame, depression and hopelessness, suicidal thoughts and feelings, feeling alienated and alone, headaches, stomach problems, chest pain and substance abuse.

It is contemplated that a composition comprising a compound of Formula I, either alone or in combination with an N-methyl D-aspartate (NMDA) pathway interrupter, will provide an effective treatment for stress. NMDA receptors belong to the glutamate receptor family. They are ligand-gated ion channels permeable to $Ca^{2+}$ and $Na^+$ ions, and are involved in synaptic plasticity, neuronal development, and learning and memory. Long-term potentiation, which is a cellular mechanism for memory, is regulated in part by NMDA receptor-mediated $Ca^{2+}$ influx. Activation of the NMDA receptor increases cAMP in the CA1 region of the hippocampus, which is mediated by $Ca^{2+}$-calmodulin-dependent adenylyl cyclase. The influx of $Ca^{2+}$ also stimulates $Ca^{2+}$-calmodulin-dependent nitric-oxide (NO) synthase (NOS) type to produce NO, which stimulates guanylyl cyclase to produce cGMP. cAMP and cGMP are involved in a number of intracellular processes such as activation of kinases, signal transduction, gene transcription, and regulation of channel function. Suvarna, et al., *J. Pharmacol. Exp. Ther.*, 302 (1):249-256 (2002). Further, NMDA signaling pathways also has regulatory effect on the Arc translation, which plays an important role in the consolidation of memory. Bloomer, et al., *J. Bio. Chem.* 283(1): 582-592 (2008). An N-methyl D-aspartate pathway interrupter can be an antagonist or inhibitor of any the receptors, enzymes, ion channels, etc. that are involved in the regulation of synaptic plasticity, neuronal development, and learning and memory in which NMDA receptors play a role.

In some embodiments, the NMDA pathway interrupter is selected from the group consisting of amantadine, dextromethorphan, dextrorphan, ethanol, ketamine, ketobemidone, memantine, methadone, nitrous oxide, phencyclidine, dizocilpine (MK801) and tramadol. In one embodiment, the NMDA pathway interrupter is cycloserine.

Dosage and Routes of Administration

It is contemplated that any route of administration and dosage form may be compatible with the compound and methods discussed above. The appropriate dosing regimen and route of administration can be readily determined by the attending clinician. In particular, a therapeutically effective amount of each of the components of the composition of this invention may be administered simultaneously or sequentially and in any order, and the components may be administered separately or as a fixed combination. The individual components of the composition can be administered separately at different times during the course of therapy or concurrently in divided or single composition forms.

Although compositions suitable for oral, intravenous or intraarterial delivery will probably be used most frequently, other routes that may be used include peroral, pulmonary, rectal, nasal, vaginal, lingual, intramuscular, intraperitoneal, intracutaneous and subcutaneous routes. In addition, it is contemplated that the composition can be administered transdermally in which drug is applied as part of a cream, gel, or patch (for examples of transdermal formulations, see U.S. Pat. Nos. 4,806,341; 5,149,538; and 4,626,539). Other dosage forms include tablets, capsules, pills, powders, aerosols, suppositories, parenterals, and oral liquids, including suspensions, solutions and emulsions. Sustained release dosage forms may also be used. All dosage forms may be prepared using methods that are standard in the art (see e.g., Remington's Pharmaceutical Sciences, 16th ed., A. Oslo editor, Easton Pa. 1980).

A compound of Formula I may be used in conjunction with any of the vehicles and excipients commonly employed in pharmaceutical preparations, e.g., talc, gum arabic, lactose, starch, magnesium stearate, cocoa butter, aqueous or non-aqueous solvents, oils, paraffin derivatives, glycols, etc. Coloring and flavoring agents may also be added to preparations, particularly to those for oral administration. Solutions can be prepared using water or physiologically compatible organic solvents such as ethanol, 1,2-propylene glycol, polyglycols, dimethylsulfoxide, fatty alcohols, triglycerides, partial esters of glycerine and the like. Parenteral compositions containing noribogaine may be prepared using conventional techniques that may include sterile isotonic saline, water, 1,3-butanediol, ethanol, 1,2-propylene glycol, polyglycols mixed with water, Ringer's solution, etc.

It is contemplated that the dosage required for treating pain may differ from the dosage required for treating addiction, however, the dosing regimen can be readily determined by the attending clinician based on the desired treatment. It is contemplated that for the treatment of pain, the dosage of a compound of Formula I administered to a patient may be from about 0.1 to about 100 mg per kg of body weight and, preferably, from about 0.1 to about 30 mg per kg of body weight. For the treatment of addiction, the dosage administered to a patient may be from about 0.1 to about 20 mg/ml.

Kit of Parts

One aspect of this invention is directed to a kit of parts comprising a composition as disclosed herein and a means for administering the composition to a patient in need thereof. The means for administration to a patient can include, for example, any one or combination of a syringe, a needle, an IV bag comprising the composition, a vial comprising the composition, etc.

Synthetic Methods

The compounds of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, Protecting Groups in Organic Synthesis, Third Edition, Wiley, N.Y., 1999, and references cited therein.

Furthermore, the compounds of this invention will typically contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures, or obvious modifications thereof, described in standard reference texts such as Fieser and Fieser's Reagents for Organic Synthesis, Volumes 1 15 (John Wiley and Sons, 1991), Rodd's Chemistry of Carbon Compounds, Volumes 1 5 and Supplementals (Elsevier Science Publishers, 1989), Organic Reactions, Volumes 1 40 (John Wiley and Sons, 1991), March's Advanced Organic Chemistry, (John Wiley and Sons, 4$^{th}$ Edition), and Larock's Comprehensive Organic Transformations (VCH Publishers Inc., 1989).

Compounds of this invention may be prepared using noribogaine, which may be prepared according to known procedures, such as by demethylating ibogaine by methods known in the art, such as reaction with boron tribromide/methylene chloride at room temperature. Schemes 1 and 2, where n and m are each independently 0, 1 or 2, and $R^2$ is as defined in any aspect or embodiment above, shows an exemplary general process for prepare compounds of this invention. Phosphate sources for the following reactions are generally known reagents or can be prepared by known procedures.

Scheme 1 below shows reaction schemes to phosphorylate the 12-hydroxyl group and optionally to diphosphorylate the 12-hydroxyl group and the indole nitrogen atom. Scheme 2 below shows reaction schemes to selectively phosphorylate the indole nitrogen atom by blocking the 12-hydroxyl group with a conventional hydroxyl protecting group. A variety of protecting groups, are useful as the Pg, as will be apparent to the skilled artisan. It is also contemplated that the indole nitrogen of noribogaine can be protected, the mono-, di- or tri-phopsphrylation carried out on the hydroxy group of noribogaine, following which, the N-protecting group is deprotected. Methods for preparing the N-protected noribogaine will be apparent to the skilled artisan in view of this disclosure.

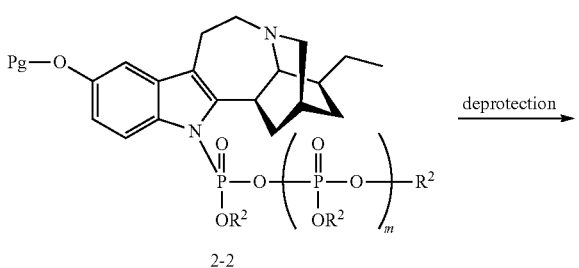

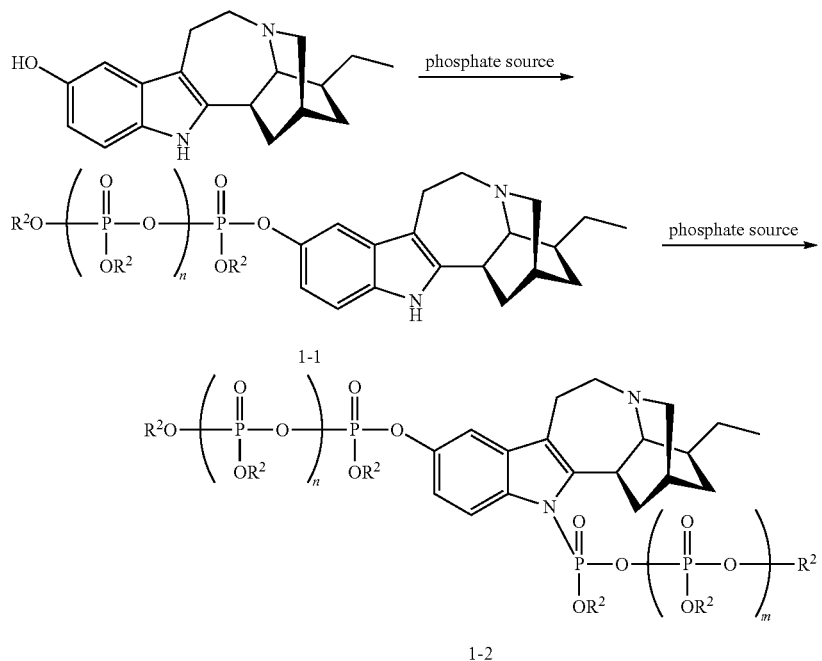

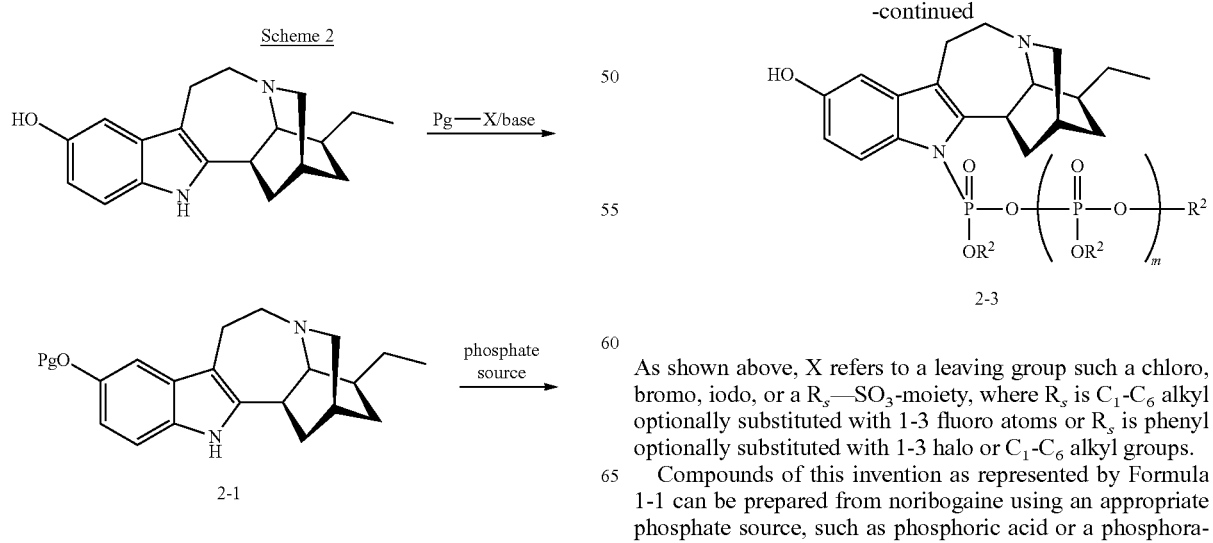

As shown above, X refers to a leaving group such a chloro, bromo, iodo, or a $R_s$—$SO_3$-moiety, where $R_s$ is $C_1$-$C_6$ alkyl optionally substituted with 1-3 fluoro atoms or $R_s$ is phenyl optionally substituted with 1-3 halo or $C_1$-$C_6$ alkyl groups.

Compounds of this invention as represented by Formula 1-1 can be prepared from noribogaine using an appropriate phosphate source, such as phosphoric acid or a phosphoramidite such as di-tert-butyl N,N-diisopropylphosphoramidite. Compounds of Formula 1-2 can be prepared from compounds of Formula 1-1 using an appropriate phosphate source under known reaction conditions. The reactions are carried out for a period of time sufficient to provide a substantial amount of the product, which can be ascertained by using routine methods such as thin layer chromatography, $^1$H-nuclear magnetic resonance (NMR) spectroscopy, and the likes. Compounds of Formula 1-1 and 1-2 can be isolated and optionally purified using standard purification techniques, such as liquid chromatography. Scheme 2 follows much of the chemistry of Scheme 1 with the exception that a blocking (protecting group—Pg) is used to avoid phosphorylation of the 12 hydroxyl group.

The dihydronoribogaine compounds of Formulas I, I-A, and II are synthesized by reducing the corresponding double bond of noribogaine. Various reducing agents well known to the skilled artisan are useful for this purpose. For example, catalytic hydrogenation employing hydrogen and a catalyst such as Pd/C or Pt/C is useful for providing the 9,17 cis, i.e. the α,α or the β,β dihydro compounds. Reagents such as borohydride or aluminum hydrides are useful for providing the α,β or the β,α dihydro compounds.

EXAMPLES

This invention is further defined by reference to the following examples. It will be apparent to those skilled in the art that many modifications, both to materials and methods, may be practiced without departing from the scope of the current invention.

| List of abbreviations and acronyms. | |
|---|---|
| Abbreviation | Meaning |
| HPLC | High Performance Liquid Chromatography |
| kg | Kilogram |
| m | Multiplet |
| M | Molar |
| M+ | Mass peak |
| Me | Methyl |
| mg | Milligram |
| MHz | Megahertz |
| mL | Milliliter |
| mM | Millimolar |
| mmol | Millimole |
| MS | Mass spectrometry |
| N | Normal |
| NMR | Nuclear magnetic resonance |
| prep | Preparative |
| q.s. | Sufficient amount |
| r.t. | Room temperature |
| s | Singlet |
| t | Triplet |
| t-Bu | tert-Butyl |
| THF | Tetrahydrofuran |
| δ | Chemical shift |

Example 1

Preparation of a Phosphate Ester of Noribogaine

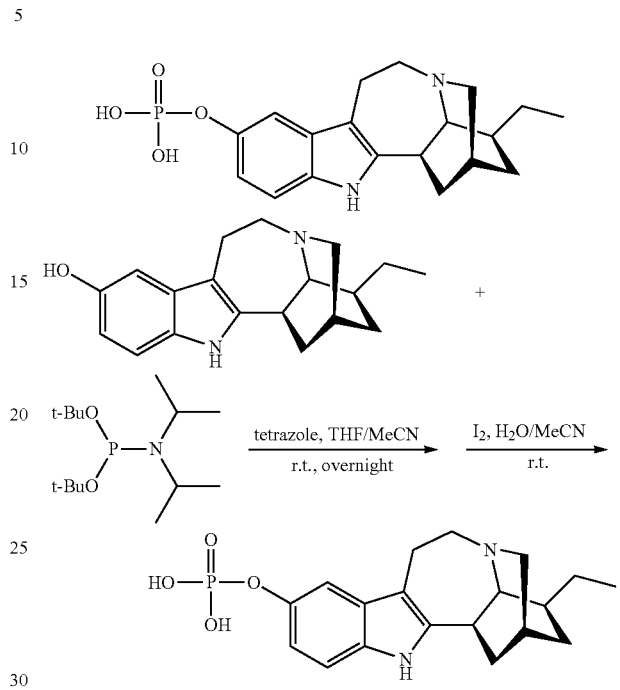

Di-tert-butyl N,N-diisopropylphosphoramidite (0.33 mL, 1.2 mmol) was added into a solution of noribogaine (90 mg, 0.3 mmol, free base) and tetrazole (2.7 mL, 1.2 mmol, 0.45 M in MeCN) in 5 mL of THF at room temperature. After 18 hours, the reaction mixture was concentrated and diluted with dichloromethane. The solution was washed with water (2×) and brine and dried over $Na_2SO_4$. The organic layer was concentrated, and the residue was dissolved in 8 mL of MeCN. Water (0.5 mL) followed by iodine (120 mg, 0.45 mmol) was added, and the resulting solution was stirred at room temperature for 7 hours before the reaction was quenched with aqueous $Na_2S_2O_3$ solution. Prep-HPLC purification afforded the monophosphate ester of noribogaine (30 mg, 26%) as an off-white solid.

MS calculated for $(C_{19}H_{25}N_2O_4P)$: 376; MS found, (M+1): 377. $^1$H NMR (300 MHz, $D_2O$) δ 8.60 (s, 1H), 7.49 (s, 1H), 7.46 (d, 1H), 7.18 (d, 1H), 3.60-3.86 (m, 3H), 3.35-3.60 (m, 5H), 2.40-2.53 (m, 1H), 2.10-2.36 (m, 3H), 1.65-1.86 (m, 3H), 1.45-1.57 (m, 1H), 1.15 (t, 3H).

Example 2

Formulations

The following ingredients are mixed intimately and pressed into single scored tablets.

| Ingredient | Quantity per tablet, mg |
|---|---|
| Phosphate Ester of Noribogaine | 40 |
| Cornstarch | 50 |
| Croscarmellose sodium | 25 |
| Lactose | 120 |
| Magnesium stearate | 5 |

The following ingredients are mixed intimately and loaded into a hard-shell gelatin capsule.

| Ingredient | Quantity per tablet, mg |
| --- | --- |
| Phosphate Ester of Noribogaine | 20 |
| Lactose, spray-dried | 148 |
| Magnesium stearate | 2 |

The following ingredients are mixed to form a suspension for oral administration (q.s.=sufficient amount).

| Ingredient | Amount |
| --- | --- |
| Phosphate Ester of Noribogaine | 1.0 g |
| Fumaric acid | 0.5 g |
| Sodium chloride | 2.0 g |
| Methyl paraben | 0.15 g |
| Propyl paraben | 0.05 g |
| Granulated sugar | 25.0 g |
| Sorbitol (70% solution) | 13.0 g |
| Veegum K (Vanderbilt Co) | 1.0 g |
| Flavoring | 0.035 mL |
| colorings | 0.5 mg |
| distilled water | q.s. to 100 mL |

The following ingredients are mixed to form an injectable formulation.

| Ingredient | Quantity per tablet, mg |
| --- | --- |
| Phosphate Ester of Noribogaine | 0.2 mg-20 mg |
| sodium acetate buffer solution, 0.4M | 2.0 mL |
| HCl (1N) or NaOH (1N) | q.s. to suitable pH |
| water (distilled, sterile) | q.s. to 20 mL |

A suppository of total weight 2.5 g is prepared by mixing the compound of the invention with Witepsol® H-15 (triglycerides of saturated vegetable fatty acid; Riches-Nelson, Inc., New York), and has the following composition:

| Ingredient | Quantity per tablet, mg |
| --- | --- |
| Phosphate Ester of Noribogaine | 500 mg |
| Witepsol ® H-15 | Balance |

Example 3

In Vivo Microdialysis in Adult Rats

A phosphate ester of noribogaine is given via a microdialysis probe in the right frontal cortex, while a probe in the left cortex serves as a vehicle control site.

Guide cannulae (CMA/12 polyurethane, Carnegie Medicine, Sweden) is implanted into the left and right frontal (motor) cortex under anesthesia. The tips of the guide are positioned at coordinates according to Paxinos and Watson, The rat brain in stereotaxic coordinates, Sydney, Academic Press, 1986. Microdialysis experiments are performed following a recovery period of at least 3 days after surgery. The microdialysis probe is lowered through the guide cannula. 14 to 16 h after insertion, perfusion of the probe can be started using Ringer solution (in mM 147 Na$^+$, 2.3 Ca$^{2+}$, 4.0 K$^+$ and 155.6 Cl$^-$, pH 6.0). Two dialysate samples are collected over a time period of 1 h before rats are injected with noribogaine. Following drug administration, further samples are collected over the next 2 h. The left microdialysis probe is perfused with the respective drug vehicle, e.g. Ringer solution.

Noribogaine concentrations in dialysate and plasma samples is determined by HPLC with UV detection.

Example 4

Treatment of PTSD

A 75 kg male patient presents with post traumatic stress disorder. The patient is treated with one of the pharmaceutical compositions of Example 2 with 10-100 mg of a NMDA receptor pathway interrupter as determined by the attending clinician. Administration is continued until the symptoms of post traumatic stress disorder are alleviated.

What is claimed is:

1. A compound of Formula I:

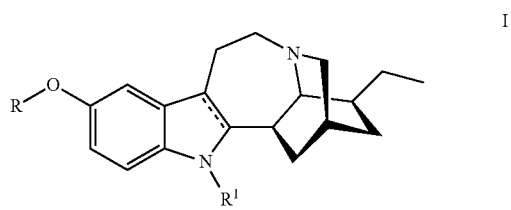

wherein:

refers to a single or a double bond provided that when is a single bond, Formula I refers to the corresponding vicinal dihydro compound;

R is hydrogen, and R$^1$ is a diphosphate or a triphosphate; or R is a monophosphate, a diphosphate or a triphosphate, and R$^1$ is hydrogen, a monophosphate, a diphosphate or a triphosphate;

provided that both R and R$^1$ are not hydrogen;

wherein one or more of the monophosphate, diphosphate and triphosphate groups of R and R$^1$ are optionally esterified with one or more C$_1$-C$_6$ alkyl esters;

or a salt thereof.

2. The compound of claim 1, wherein R is a monophosphate.

3. The compound of claim 1, wherein R$^1$ is hydrogen.

4. The compound of claim 1, wherein R is a monophosphate and R$^1$ is hydrogen.

5. A pharmaceutical composition comprising a therapeutically effective amount of the compound of claim 1 and at least a pharmaceutically acceptable excipient.

6. A pharmaceutical composition comprising at least a pharmaceutically acceptable excipient and a therapeutically effective amount of a compound of Formula II:

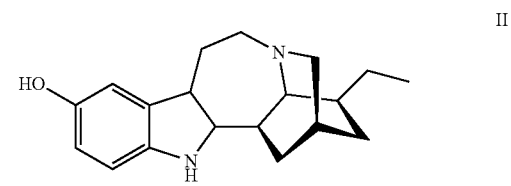

or pharmaceutically acceptable salts thereof.

7. A method for treating pain in a patient which method comprises administering to said patient a therapeutically effective amount of the compound of claim 1.

* * * * *